United States Patent
Berlinger et al.

(10) Patent No.: US 11,645,768 B2
(45) Date of Patent: May 9, 2023

(54) MULTI IMAGE FUSION BASED POSITIONING VERIFICATION

(71) Applicant: Brainlab AG, Munich (DE)

(72) Inventors: Kajetan Berlinger, Munich (DE); Michael Stead, Unterhaching (DE)

(73) Assignee: BRAINLAB AG, Munich (DE)

( * ) Notice: Subject to any disclaimer, the term of this patent is extended or adjusted under 35 U.S.C. 154(b) by 557 days.

(21) Appl. No.: 16/091,377

(22) PCT Filed: Feb. 7, 2018

(86) PCT No.: PCT/EP2018/053100
§ 371 (c)(1),
(2) Date: Oct. 4, 2018

(87) PCT Pub. No.: WO2018/153675
PCT Pub. Date: Aug. 30, 2018

(65) Prior Publication Data
US 2019/0156478 A1 May 23, 2019

Related U.S. Application Data

(63) Continuation-in-part of application No. PCT/EP2017/054323, filed on Feb. 24, 2017.

(51) Int. Cl.
*G06T 7/33* (2017.01)
*G06T 7/30* (2017.01)
(Continued)

(52) U.S. Cl.
CPC .............. *G06T 7/33* (2017.01); *A61B 5/0077* (2013.01); *A61B 5/7292* (2013.01); *A61B 34/10* (2016.02);
(Continued)

(58) Field of Classification Search
CPC combination set(s) only.
See application file for complete search history.

(56) References Cited

U.S. PATENT DOCUMENTS 7,720,196 B2    5/2010  Zhang et al.
2003/0016853 A1*  1/2003  Oosawa .................. G06T 7/337
                                            382/209
(Continued)

FOREIGN PATENT DOCUMENTS

EP       2239010 B1      6/2013
WO    WO2013009427 A2    1/2013

OTHER PUBLICATIONS

Borst et al. "Clinical Results for Image-Guided Deep Inspiration Breath Hold Breast Irradiation" International Journal of Radiation: Oncology Biology Physics, Pergamon Press. vol. 78, No. 5. Dec. 1, 2010.

(Continued)

*Primary Examiner* — Zhiyu Lu
(74) *Attorney, Agent, or Firm* — Gray Ice Higdon (57) ABSTRACT

The present invention involves positionally identifying several anatomical structures of interest of a patient's anatomy on images which have been acquired at different points of time. For each anatomical structure a separate image fusion transformation between these images is performed. For at least one of the image fusion transformations it is then determined whether this transformation is within a predetermined threshold, wherein for this determination, at least one further image fusion transformation of another anatomical structure is taken into account.

13 Claims, 2 Drawing Sheets

(51) Int. Cl.
  *G06T 7/73* (2017.01)
  *G06T 7/246* (2017.01)
  *A61B 5/00* (2006.01)
  *A61N 5/10* (2006.01)
  *A61B 34/10* (2016.01)
  *G16H 30/40* (2018.01)
  *G06T 7/00* (2017.01)
  *G06T 11/00* (2006.01)
  *A61B 90/00* (2016.01)

(52) U.S. Cl.
  CPC ......... *A61N 5/1037* (2013.01); *A61N 5/1039* (2013.01); *A61N 5/1049* (2013.01); *G06T 7/0014* (2013.01); *G06T 7/248* (2017.01); *G06T 7/251* (2017.01); *G06T 7/30* (2017.01); *G06T 7/74* (2017.01); *G06T 7/75* (2017.01); *G06T 11/003* (2013.01); *G16H 30/40* (2018.01); *A61B 2034/107* (2016.02); *A61B 2090/3762* (2016.02); *A61N 2005/1059* (2013.01); *G06T 2207/10072* (2013.01); *G06T 2207/10081* (2013.01); *G06T 2207/10116* (2013.01); *G06T 2207/20128* (2013.01); *G06T 2207/20221* (2013.01); *G06T 2207/30008* (2013.01); *G06T 2207/30081* (2013.01); *G06T 2207/30096* (2013.01); *G06T 2207/30196* (2013.01)

(56) References Cited

U.S. PATENT DOCUMENTS

| | | | | |
|---|---|---|---|---|
| 2008/0266325 | A1* | 10/2008 | Niu | G06T 13/80 345/646 |
| 2009/0187112 | A1 | 7/2009 | Meir et al. | |
| 2010/0202673 | A1 | 8/2010 | Zhang et al. | |
| 2011/0305405 | A1* | 12/2011 | Kawamura | G06T 7/337 382/294 |
| 2013/0016889 | A1* | 1/2013 | Myronenko | G06T 7/337 382/128 |
| 2013/0287167 | A1 | 10/2013 | Gum et al. | |
| 2015/0302608 | A1 | 10/2015 | Vilsmeier et al. | |
| 2015/0335915 | A1* | 11/2015 | Berlinger | A61N 5/1037 600/1 |
| 2018/0056090 | A1* | 3/2018 | Jordan | A61N 5/107 |
| 2018/0056091 | A1* | 3/2018 | Jordan | A61N 5/107 |

OTHER PUBLICATIONS

Wong et al. "Real-Time Monitoring and Control on Deep Inspiration Breath-Hold for Lung Cancer Radiotherapy-Combination of ABC and External marker Tracking" Medical Physics vol. 37, No. 9. Aug. 16, 2010.

Gardner et al. "Tumor Localization, Disimetry, Simulation and Treatment Procedures for Radiotherapy: the Isocentric Technique" Department of Radiology, Stanford university of Medicine. Jan. 1, 1972.

Latty et al. "Review of Deep Inspiration Breath-Hold Techniques for the Treatment of Breast Cancer" Journal of Medical Radiation Sciences. Jan. 12, 2015.

Mittauer et al. "Monitoring ABC-assisted deep inspiration breath hold for left-sided breast radiotherapy with an optical tracking system" Medical Physics, vol. 42, No. 1. Jan. 1, 2015.

D'Souza et al. "Real-time intra-fraction-motion tracking using the treatment couch: a feasibility study; Couch-based motion synchronized radiation delivery" Physics in Medicine and Biology, vol. 50, No. 17. Sep. 7, 2005.

Nehmeh et al. "Deep-Inspiration Breath-Hold PET/CT of the Thorax" The Journal of Nuclear Medicine. Jan. 1, 2007.

Gikas et al. "Deep inspiration breath hold and respiratory gating strategies for reducing organ motion in radiation treatment" Seminars in Radiation Onco, vol. 14, No. 1. Jan. 1, 2004.

International Search Report and Written Opinion issued in PCT/EP2018/053100 dated Apr. 20, 2018.

Xing et al. "Overview of Image-Guided Radiation Therapy". Medical Dosim, vol. 31, No. 2. May 9, 2006.

* cited by examiner

MULTI IMAGE FUSION BASED POSITIONING VERIFICATION

FIELD OF THE INVENTION

The present invention relates to a computer-implemented method for verifying relative positions of a plurality of anatomical structures of interest of a patient, a corresponding computer program, a non-transitory program storage medium storing such a program and a computer for executing the program, as well as a medical system comprising an electronic data storage device and the aforementioned computer.

TECHNICAL BACKGROUND

For medical procedures performed on a patient, such as image guided surgery, radiotherapy or even image based diagnostics it is desirable to know the spatial position (including the spatial location and/or the spatial orientation), and preferably even the size and the shape of anatomical structures of interest of the patient's body. While some anatomical structures maintain their position over time, some structures do not as they are subject to the patient's respiratory motion. The problem which arises in this context is that some medical procedures are planned on the basis of images that show certain anatomical structures of interest, but which have been acquired prior to the actual medical procedure. Thus, it has to be ensured that the anatomical structures of interest are arranged in the same manner for the medical procedure, as they were when the planning image was acquired.

Radiotherapy of breast cancer as a particular example of such medical procedures starts in most cases with a resection of the tumor, which is then followed by the actual radiation therapy. Clinical studies have shown that irradiating the tumor bed reduces the risk of recurrence dramatically.

As the heart, especially the RIVA (Ramus interventricularis anterior) is very sensitive to radiation, such that unintended irradiation of the heart may yield in the long term to heart diseases, special care has to be taken to safe the heart from radiation. This problem particularly arises for treatment of the left breast, as the distance from the radiotherapy target to the heart is comparatively short. Therefore, most procedures are planned and performed in the state of a so-called "DIBH" (deep inspiration breath-hold). With an increased inspiration the heart moves away from the radiotherapy target in an inferior and posterior direction, and therefore moves out of the radiation beam's path. The patient is coached to perform a DIBH during a pre-therapy CT-scan, on which basis the treatment plan is created. During the following treatment, the patient is again coached to reproduce the DIBH as close as possible to the one that was existent when the CT-scan was made. In order to verify that the DIBH is performed correctly during treatment, medical personnel manually checks the position of the anatomical structures of interest on X-ray-images or EPID-images that are acquired during the treatment-DIBH.

The present invention has the object of improving the verification of relative positions of anatomical structures of interest, particularly for verifying that a deep inspiration breath-hold procedure is correctly performed.

The present invention can be used for radiotherapy procedures e.g. in connection with a system for image-guided radiotherapy such as VERO® and ExacTrac®, both products of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The present invention involves identifying several anatomical structures of interest of a patient's anatomy on images which have been acquired at different points in time. For each anatomical structure a separate image fusion transformation between these images is performed. For at least one of the image fusion transformations it is then determined whether this transformation is within a predetermined threshold, wherein for this determination, at least one further image fusion transformation of another anatomical structure is taken into account.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method for verifying a relative position of a plurality of anatomical structures of interest of a patient The method comprises executing, on at least one processor of at least one computer (for example at least one computer being part of the navigation system), the following exemplary steps which are executed by the at least one processor:

a) planning data is acquired, describing at least one planning-image showing the plurality of anatomical structures;
b) first identification data is determined based on the planning data, describing a position and/or shape of at least two of the plurality of anatomical structures of interest within the at least one planning-image;
c) verification data is acquired describing at least one verification-image showing the least two of the plurality of anatomical structures of interest;
d) second identification data is determined based on the verification data, particularly based on the verification data and the first identification data, describing a position and/or shape of the at least two of the plurality of the anatomical structures of interest within the at least one verification-image;
e) transformation data is determined based on the first identification data and the second identification data, describing, for each one of the at least two anatomical structures, a distinct image fusion transformation; and
f) evaluation data is determined based on the transformation data, describing, for at least one first image fusion transformation, whether the at least one first image fusion transformation is within a predetermined threshold, thereby taking into account at least one second image fusion transformation.

The first step of acquiring planning data for example involves an image acquisition procedure where one or more planning-images of the patient's anatomy are made, which show the later anatomical structures of interest. Based on this at least one planning-image the later treatment is planned. For example, the at least one planning-image may show parts of the patient's rib cage including the spine, the heart and at least one of the patient's sternum and the anterior sections of the patient's ribs.

In the context of breast cancer radiotherapy, the anterior parts of the ribs as well as the sternum indicate the spatial position of the later treatment target, namely the patient's breast, as this is located outside the patient's chest on the anterior sections of the ribs. The patient's heart, on the other hand, represents a further anatomical structure of interest as it has to be spared from radiation. Thus, it is important that a treatment beam does not cross the heart. A further anatomical structure of interest may be the patient's spine. This is because some patients unintendedly "use the spine" to perform a deep inspiration breath hold. As this movement, contrary to a correctly performed deep inspiration breath hold, does not move the heart out of the beam path, it has to be avoided during treatment. Moreover, the relative position between the spine and the sternum/the anterior sections of the ribs gives an indication about the depth of the deep inspiration breath hold and should of course be similar for all DIBHs performed prior to and during treatment.

While the above described anatomical structures of interest are of particular interest when performing a DIBH procedure, other anatomical structures may be of interest for other procedures. Generally, the inventive method may be performed to verify a correct posture and/or positioning of the patient for any medical procedure. The term "posture" is to be understood to have impact on the relative position of the anatomical structures of interest, such as the respiration depth or DIBH-performance of the patient. The term "positioning" describes the patient's spatial position with respect to medical equipment, for example with respect to an isocentre of a radiation treatment apparatus. As a further specific example, the inventive method is used to verify a correct positioning of the patient (for example with respect to a treatment apparatus) for prostate imaging or prostate cancer radiotherapy. In this specific case one of, the anatomical structures of interest is of course the patient's prostate. The patient's rectum is, just like the aforementioned heart, an anatomical structure which is sensitive to radiation and which should therefore be kept out of the path of a radiotherapy treatment beam. The same applies to the patient's spine which therefore may represent a further anatomical structure.

Once the planning data has been acquired by creating one or more planning images of the anatomical structures of interest, the method comprises, as a second step, that at least two anatomical structures of interest are identified on the one or more planning images. For example, a practitioner may manually mark the outline of the anatomical structures on the at least one planning image. On the other hand, a computer system having access to an anatomical atlas may support or even fully automatically perform such identification process.

After the anatomical structures of interest have been identified on the pre-treatment images (which may include the spatial location, the spatial orientation, the shape and/or the size of the anatomical structures), on which basis the oncoming medical procedure is planned, it is of course desirable that during the following medical procedure, the anatomical structures maintain their relative positions as shown on the planning image.

Therefore, verification data is acquired by creating at least one verification image of the anatomical structures of interest during the medical procedure. For breast cancer radiotherapy, the one or more verification images are made during the DIBHs are performed. Again, the anatomical structures of interest are then identified on the one or more verification images. This may again be done manually by a practitioner with or without support from the above computer system. Further, the anatomical structures may also be identified on the verification images by taking into account the already performed identification on the planning images.

As soon as the anatomical structures of interest have been identified on both, the planning images and the verification images, an image fusion transformation can be performed separately for each anatomical structure. The separately determined transformations for each one of the structures then indicate how much the state of each one of the anatomical structures has changed between the planning images and the verification images. Ideally, the state of each one of the anatomical structures has not changed at all, which means that, while the medical procedure is performed, the anatomical structures are arranged in the same manner as they were when the planning image was made. In turn, this verifies that the medical procedure is performed according to plan.

However, it is likely that the image fusion transformation shows that the state of a particular anatomical structure has changed and therefore deviated from it's original state that is shown on the planning image. While this may be acceptable within a predetermined threshold for such deviations, a larger deviation beyond the predetermined threshold could indicate that the patient's position, for example the patient's DIBH is not performed correctly and is therefore unacceptable for starting or continuing the medical procedure.

With the present invention however, it is possible to distinguish between an unallowable posture of the patient on the one hand, which may be for example an incorrectly performed DIBH as compared to the treatment plan, and on the other hand an incorrect overall placement of the patient with respect to the medical equipment including the image device for acquiring the verification images.

This is done by taking into account an image fusion transformation for another anatomical structure of interest when evaluating acceptability of the image fusion transformation in question. If, for example, the more than one image fusion transformation indicates the same or a similar deviation for more than one anatomical structure of interest, or even all anatomical structures of interest, a strong indication is on hand that the entire patient is incorrectly positioned with respect to the medical apparatus, while the posture of the patient itself may be correct.

An incorrect overall position of the patient can be easily corrected for. On the basis of one of the anatomical structures of interest which is defined as a main anatomical structure, the patient is positioned with respect to the medical equipment including the imaging device for acquiring the verification images. Preferably, it is the image fusion transformation of this structure (denoted as "main anatomical structure"), which is taken into account when evaluating the one or more image fusion transformations for the remaining anatomical structures of interest.

In the context of breast cancer radiotherapy, it is the sternum and/or the anterior section of at least one rib of the patient which is defined as this main anatomical structure.

In an example of the method according to the first aspect, at least one second image fusion transformation is taken into account for evaluating at least one first image fusion transformation. More specifically, at least one second image fusion transformation is applied to at least one first image fusion transformation. In other words, the image fusion transformation for any anatomical structure of interest may be used for determining whether the image transformation of any other anatomical structure of interest is acceptable, i.e. is within a predetermined threshold. In a particular example of the invention, a transformation matrix of at least one first image fusion transformation is multiplied with the inverse transformation matrix of at least one second image fusion transformation.

Further, as already indicated further above, any anatomical structure of interest including the main anatomical structure of interest may be used to position the patient with respect to the medical equipment. In this respect, position data is determined based on the second identification data, describing for at least one of the anatomical structures of interest, particularly the main anatomical structure of interest, whether it is positioned at a predefined desired position with respect to a radiation treatment apparatus, particularly with respect to one or more treatment beams. In case this constraint is not met, a signal may be issued which is designated to warn personal and/or shut off a radiation treatment apparatus generating one or more treatment beams in case at least one of the anatomical structures of interest is not positioned at the predefined desired position. Moreover, reposition data may be determined based on the second identification data, describing for at least one of the anatomical structures of interest, particularly the main anatomical structure of interest, the positional deviation from a predefined desired position with respect to a radiation treatment apparatus, particularly with respect to one or more treatment beams. Again, a signal may be issued which is designated to reposition the patient with respect to the radiation treatment apparatus for positioning the at least one of the anatomical structures of interest at a predefined desired position.

In any case, a signal may be issued which is designated to warn personal and/or shut off a radiation treatment apparatus generating one or more treatment beams in case the predetermined threshold for at least one of the image fusion transformations is exceeded, particularly for the time period the predetermined threshold is exceeded.

Further, the planning images may include at least one CT-image of the patient, wherein the verification images may include at least one monoscopic X-ray-image and/or at least one stereoscopic X-ray-image-pair.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program.

In a third aspect, the invention is directed to a non-transitory computer-readable program storage medium on which the program according to the fourth aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical system, comprising:
  a) the at least one computer according to the fourth aspect;
  b) at least one electronic data storage device storing at least the planning data and the verification data; and
  c) a medical device for carrying out a medical procedure on the patient,
    wherein the at least one computer is operably coupled to
    the at least one electronic data storage device for acquiring, from the at least one data storage device, at least the planning data and the verification data, and
    the medical device for issuing a control signal to the medical device for controlling the operation of the medical device on the basis of at least the evaluation data.

In an example of the system according to the fifth aspect, the medical device comprises a radiation treatment apparatus comprising a treatment beam source and a patient support unit (such as at least one of a patient bed or a headrest). The at least one computer is then operably coupled to the radiation treatment apparatus for issuing a control signal to the radiation treatment apparatus for controlling, on the basis of at least the evaluation data, at least one of
  the operation of the treatment beam source or
  the position of the patient support unit.

The invention does not involve or in particular comprise or encompass any surgical or therapeutic activity. The invention is instead directed as applicable to verify a relative position of anatomical structures on the basis of images of the patient's anatomy. For this reason alone, no surgical or therapeutic activity and in particular no surgical or therapeutic step is necessitated or implied by carrying out the invention.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The information on the imaging geometry preferably comprises information which allows the analysis image (x-ray image) to be calculated, given a known relative position between the imaging geometry analysis apparatus and the analysis object (anatomical body part) to be analysed by x-ray radiation, if the analysis object which is to be analysed is known, wherein "known" means that the spatial geometry (size and shape) of the analysis object is known. This means for example that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The location and in particular orientation of the imaging geometry is for example defined by the position of the x-ray device, for example by the position of the x-ray source and the x-ray detector and/or for example by the position of the multiplicity (manifold) of x-ray beams which pass through the analysis object and are detected by the x-ray detector. The imaging geometry for example describes the position (i.e. the location and in particular the orientation) and the shape (for example, a conical shape exhibiting a specific angle of inclination) of said multiplicity (manifold). The position can for example be represented by the position of an x-ray beam which passes through the centre of said multiplicity or by the position of a geometric object (such as a truncated cone) which represents the multiplicity (manifold) of x-ray beams. Information concerning the above-mentioned interaction is preferably known in three dimensions, for example from a three-dimensional CT, and describes the interaction in a spatially resolved way for points and/or regions of the analysis object, for example for all of the points and/or regions of the analysis object. Knowledge of the imaging geometry for example allows the location of a source of the radiation (for example, an x-ray source) to be calculated relative to an image plane (for example, the plane of an x-ray detector). With respect to the connection between three-dimensional analysis objects and two-dimensional analysis images as defined by the imaging geometry, reference is made for example to the following publications:

1. "An Efficient and Accurate Camera Calibration Technique for 3D Machine Vision", Roger Y. Tsai, Proceedings of the IEEE Conference on Computer Vision and Pattern Recognition. Miami Beach, Fla., 1986, pages 364-374
2. "A Versatile Camera Calibration Technique for High-Accuracy 3D Machine Vision Metrology Using Off-the-Shelf TV Cameras and Lenses", Roger Y. Tsai, IEEE Journal of Robotics and Automation, Volume RA-3, No. 4, August 1987, pages 323-344.

3. "Fluoroscopic X-ray Image Processing and Registration for Computer-Aided Orthopedic Surgery", Ziv Yaniv
4. EP 08 156 293.6
5. U.S. 61/054,187

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

The movements of the treatment body parts are for example due to movements which are referred to in the following as "vital movements". Reference is also made in this respect to EP 2 189 943 A1 and EP 2 189 940 A1, also published as US 2010/0125195 A1 and US 2010/0160836 A1, respectively, which discuss these vital movements in detail. In order to determine the position of the treatment body parts, analytical devices such as x-ray devices, CT devices or MRT devices are used to generate analytical images (such as x-ray images or MRT images) of the body. For example, analytical devices are constituted to perform medical imaging methods. Analytical devices for example use medical imaging methods and are for example devices for analysing a patient's body, for instance by using waves and/or radiation and/or energy beams, for example electromagnetic waves and/or radiation, ultrasound waves and/or particles beams. Analytical devices are for example devices which generate images (for example, two-dimensional or three-dimensional images) of the patient's body (and for example of internal structures and/or anatomical parts of the patient's body) by analysing the body. Analytical devices are for example used in medical diagnosis, for example in radiology. However, it can be difficult to identify the treatment body part within the analytical image. It can for example be easier to identify an indicator body part which correlates with changes in the position of the treatment body part and for example the movement of the treatment body part. Tracking an indicator body part thus allows a movement of the treatment body part to be tracked on the basis of a known correlation between the changes in the position (for example the movements) of the indicator body part and the changes in the position (for example the movements) of the treatment body part. As an alternative to or in addition to tracking indicator body parts, marker devices (which can be used as an indicator and thus referred to as "marker indicators") can be tracked using marker detection devices. The position of the marker indicators has a known (predetermined) correlation with (for example, a fixed relative position relative to) the position of indicator structures (such as the thoracic wall, for example true ribs or false ribs, or the diaphragm or intestinal walls, etc.) which for example change their position due to vital movements.

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcare_us_elekta_vmat.php and http://www.varian.com/us/oncology/treatments/treatment_techniques/rapidarc.

A treatment body part can be treated by one or more treatment beams issued from one or more directions at one or more times. The treatment by means of the at least one treatment beam thus follows a particular spatial and temporal pattern. The term "beam arrangement" is then used to cover the spatial and temporal features of the treatment by means of the at least one treatment beam. The beam arrangement is an arrangement of at least one treatment beam.

The "beam positions" describe the positions of the treatment beams of the beam arrangement. The arrangement of beam positions is referred to as the positional arrangement. A beam position is preferably defined by the beam direction and additional information which allows a specific location, for example in three-dimensional space, to be assigned to the treatment beam, for example information about its co-ordinates in a defined co-ordinate system. The specific location is a point, preferably a point on a straight line. This line is then referred to as a "beam line" and extends in the beam direction, for example along the central axis of the treatment beam. The defined co-ordinate system is preferably defined relative to the treatment device or relative to at least a part of the patient's body. The positional arrangement comprises and for example consists of at least one beam position, for example a discrete set of beam positions (for example, two or more different beam positions), or a continuous multiplicity (manifold) of beam positions.

For example, one or more treatment beams adopt(s) the treatment beam position(s) defined by the positional arrangement simultaneously or sequentially during treatment (for example sequentially if there is only one beam source to emit a treatment beam). If there are several beam sources, it is also possible for at least a subset of the beam positions to be adopted simultaneously by treatment beams during the treatment. For example, one or more subsets of the treatment beams can adopt the beam positions of the positional arrangement in accordance with a predefined sequence. A subset of treatment beams comprises one or more treatment beams. The complete set of treatment beams which comprises one or more treatment beams which adopt(s) all the beam positions defined by the positional arrangement is then the beam arrangement.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
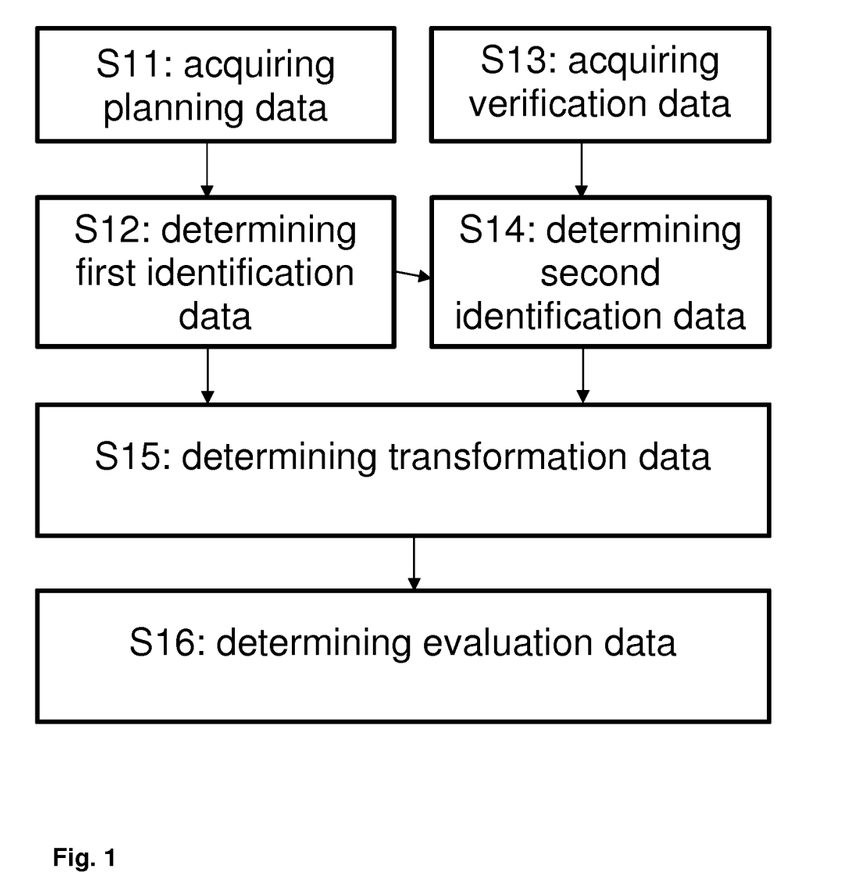
FIG. 1 illustrates the basic steps of the method in accordance with the first aspect of the present invention.

FIG. 1 illustrates the basic steps of the method according to the first aspect. The inventive method starts off with step S11 which encompasses the acquisition of a CT-dataset that provides the one or more planning images. In the case of breast cancer radiotherapy, the planning image shows the anatomical structures in the state of a DIBH the patient performs prior to the actual radiotherapy treatment.

In step S12, the anatomical structures of interest are determined/marked within the planning image. For breast cancer radiotherapy, the anatomical structures of interest may include the sternum and/or the anterior sections of the patient's ribs as an indicator for the position of the breast tumour bed to be irradiated, the spine of the patient as an indicator of whether the DIBH is performed correctly without the patient "making use of the spine", and of course the heart as a radiation sensitive structure which should be spared from radiation. Thus, the arrangement of the anatomical structures for an ideal DIBH is known, on the basis of which a treatment plan is generated. Consequently, further DIBHs of the patient during treatment should resemble this first one as far as possible.

After the patient has been positioned with respect to the radiation treatment apparatus, further verification images are made (Step S13) so as to evaluate a correct positioning of the patient with respect to the radiation treatment apparatus as well as whether the patient performs a DIBH correctly, i.e. in the same manner as the first one, such that the anatomical structures are arranged in the same manner as in the planning image that forms the basis for the treatment plan.

To do so, the anatomical structures of interest which have been determined/marked in the planning image are determined/marked in the verification image(s), as well (Step S14). This second identification procedure is supported by data that has already been acquired during the first identification procedure. For example, a computer system may locate the anatomical structure in the verification image by searching the verification image for image content which resembles the anatomical structures determined/marked in the planning image.

In the following step S15, a separate image fusion is performed for each anatomical structure which has been determined/marked in both, the planning image and the verification image. This delivers a separate transformation matrix for each anatomical structure. In case a previously designated main anatomical structure which is used for aligning the patient with respect to the radiation treatment apparatus is positioned similarly in both, the planning image and the verification image, it can be assumed that the patient is positioned as desired with respect to the radiation treatment apparatus. In case this also applies for the remaining anatomical structures, it is further assumed that the patient performs the DIBH correctly. However, in case at least one of the remaining anatomical structures has a deviating position as compared to the planning image, it is likely that the patient does not perform the DIBH as desired. In case the deviation exceeds a certain threshold, particularly when a sensitive structure such as the heart lies within the beam path, a signal may be output to warn personal or even pause/abort the treatment procedure. In case each one of the anatomical structures deviates in the same manner as compared to the planning image, even beyond a predetermined threshold of allowability, it can be assumed that the patient performs the DIBH in a correct and desired manner, but is not aligned properly with respect to the radiation therapy apparatus. Distinguishing between the aforementioned cases is possible as, in accordance with the present invention, the image fusion transformations that have been calculated for each one of the anatomical structures separately, are compared to each other and taken into account when evaluating the image fusion transformation of a specific anatomical structure.

Figure 2:
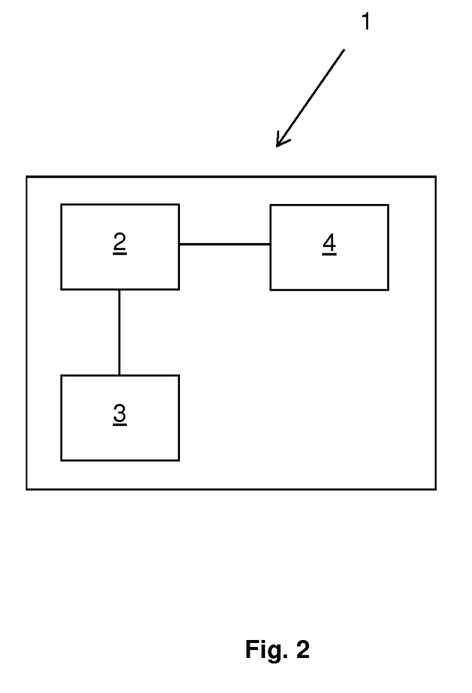
FIG. 2 is a schematic illustration of the system according to the fifth aspect.

FIG. 2 is a schematic illustration of the medical system 1 according to the fifth aspect. The system is in its entirety identified by reference sign 1 and comprises a computer 2, an electronic data storage device (such as a hard disc) 3 for storing at least the patient data and a medical device 4 (such as a radiation treatment apparatus). The components of the medical system 1 have the functionalities and properties explained above with regard to the fifth aspect of this disclosure.

The invention claimed is:

1. A computer-implemented method for verifying a relative position of a plurality of anatomical structures of interest of a patient, the method comprising:
   acquiring planning data describing at least one planning-image showing the plurality of anatomical structures;
   determining first identification data based on the planning data describing a position and/or shape of at least two of the plurality of anatomical structures of interest within the at least one planning-image, the at least two of the anatomical structures including a first anatomical structure and a second anatomical structure;
   acquiring verification data describing at least one verification-image showing the least two of the plurality of anatomical structures of interest;
   determining second identification data based on the verification data, describing a position and/or shape of the at least two of the plurality of anatomical structures of interest within the at least one verification-image;
   determining transformation data based on the first identification data and the second identification data, describing, for each one of the at least two anatomical structures, a distinct image fusion transformation, wherein a first image fusion transformation is determined for the first anatomical structure, and a second image fusion transformation is determined for the second anatomical structure, the first image fusion transformation and the second image fusion transformation being separate from each other; and
   determining evaluation data based on the transformation data, wherein the first image fusion transformation and the second image fusion transformation are applied to each other to calculate whether a deviation of one of the first anatomical structure and the second anatomical structure from its position and/or shape shown in the at least one planning-image is within a predetermined threshold, the threshold being defined based on a deviation of the other of the first anatomical structure and the second anatomical structure from its position and/or shape shown in the at least one planning-image.

2. The method according to claim 1, wherein the method is performed to verify a correct execution of a deep-inspiration-breath-hold (DIBH) procedure, wherein the at least two anatomical structures of interest are each at least one of:
   a sternum of the patient and/or an anterior section of at least one of the ribs of the patient;
   a spine of the patient;
   a heart of the patient as a sensitive structure radiation should not be applied to.

3. The method according to claim 1, wherein the method is performed to verify a correct positioning of the patient for prostate imaging or prostate cancer radiotherapy, wherein the at least two anatomical structures of interest are each at least one of:
   a prostate of the patient;
   the spine of the patient;
   a rectum of the patient as a sensitive structure radiation should not be applied to.

4. The method according to claim 1, wherein the second anatomical structure is defined as a main anatomical structure of interest, and wherein the second image fusion transformation for the main anatomical structure of interest represents the second image fusion transformation.

5. The method according to claim 4 wherein a sternum and/or an anterior section of the at least one of the ribs is defined as the main anatomical structure.

6. The method according to claim 1, wherein the determining evaluation data for the second image fusion transformation for the first anatomical structure involves applying the second image fusion transformation to the first image fusion transformation.

7. The method according to claim 6, wherein a transformation matrix of the first image fusion transformation is multiplied with the inverse transformation matrix of the second image fusion transformation.

8. The method according to claim 1, wherein a signal is issued designated to warn personnel and/or shut off a radiation treatment apparatus generating one or more treatment beams in case the predetermined threshold for at least one of the first or the second image fusion transformations is exceeded, particularly wherein the signal is issued for the time period the predetermined threshold is exceeded.

9. The method according to claim 1, wherein acquiring planning data involves acquiring one or more CT-images of the patient.

10. The method according to claim 1, wherein acquiring verification data involves acquiring one or more monoscopic X-ray-images and/or one or more stereoscopic X-ray-image-pairs.

11. A non-transitory computer-readable storage medium storing a computer program which, when executed on at least one processor of at least one computer, causes the at least one computer to perform the steps comprising:
   acquiring planning data describing at least one planning-image showing a plurality of anatomical structures;
   determining first identification data based on the planning data describing a position and/or shape of at least two of the plurality of anatomical structures of interest within the at least one planning-image, the at least two of the anatomical structures including a first anatomical structure and a second anatomical structure;

acquiring verification data describing at least one verification-image showing the least two of the plurality of anatomical structures of interest;

determining second identification data based on the verification data, describing a position and/or shape of the at least two of the plurality of the anatomical structures of interest within the at least one verification-image;

determining transformation data based on the first identification data and the second identification data, describing, for each one of the at least two anatomical structures, a distinct image fusion transformation, wherein a first image fusion transformation is determined for the first anatomical structure, and a second image fusion transformation is determined for the second anatomical structure, the first image fusion transformation and the second image fusion transformation being separate from each other; and determining evaluation data based on the transformation data, wherein the first image fusion transformation and the second image fusion transformation are applied to each other to calculate whether a deviation of one of the first anatomical structure and the second anatomical structure from its position and/or shape shown in the at least one planning-image is within a predetermined threshold, the threshold being defined based on a deviation of the other of the first anatomical structure and the second anatomical structure from its position and/or shape shown in the at least one planning-image.

12. A system for verifying a relative position of a plurality of anatomical structures of interest of a patient, comprising:

at least one computer having at least one processor and associated memory, the memory having instructions that when executed, perform the steps of;

acquiring planning data describing at least one planning-image showing the plurality of anatomical structures;

determining first identification data based on the planning data describing a position and/or shape of at least two of the plurality of anatomical structures of interest within the at least one planning-image, the at least two of the anatomical structures including a first anatomical structure and a second anatomical structure;

acquiring verification data describing at least one verification-image showing the least two of the plurality of anatomical structures of interest;

determining second identification data based on the verification data, describing a position and/or shape of the at least two of the plurality of the anatomical structures of interest within the at least one verification-image;

determining transformation data based on the first identification data and the second identification data, describing, for each one of the at least two-anatomical structures, a distinct image fusion transformation, wherein a first image fusion transformation is determined for the first anatomical structure, and a second image fusion transformation is determined for the second anatomical structure, the first image fusion transformation and the second image fusion transformation being separate from each other;

determining evaluation data based on the transformation data, wherein the first image fusion transformation and the second image fusion transformation are applied to each other to calculate whether a deviation of one of the first anatomical structure and the second anatomical structure from its position and/or shape shown in the at least one planning-image is within a predetermined threshold, the threshold being defined based on a deviation of the other of the first anatomical structure and the second anatomical structure from its position and/or shape shown in the at least one planning-image; and the at least one computer operable to issue a control signal to a medical device on the basis of at least the evaluation data.

13. The system according to the claim 12, wherein the medical device comprises:

a radiation treatment apparatus comprising a treatment beam source and a patient support unit, wherein the at least one computer is operably coupled to the radiation treatment apparatus for issuing a control signal to the radiation treatment apparatus for controlling, on the basis of at least the evaluation data, at least one of the operation of the treatment beam source or the position of the patient support unit.

* * * * *